United States Patent [19]

Taherian et al.

[11] Patent Number: 5,485,743
[45] Date of Patent: Jan. 23, 1996

[54] MICROWAVE DEVICE AND METHOD FOR MEASURING MULTIPHASE FLOWS

[75] Inventors: M. Reza Taherian, Ridgefield; Tarek M. Habashy, Danbury, both of Conn.

[73] Assignee: Schlumberger Technology Corporation, New York, N.Y.

[21] Appl. No.: 311,080

[22] Filed: Sep. 23, 1994

[51] Int. Cl.$^6$ .................................................. G01N 22/00
[52] U.S. Cl. ........................................ 73/61.44; 324/637
[58] Field of Search ........................... 73/61.41, 61.43, 73/61.44, 861.04, 861.08, 861.11; 324/637, 640

[56] References Cited

U.S. PATENT DOCUMENTS

| | | | |
|---|---|---|---|
| 3,551,806 | 12/1970 | Sasaki | 324/640 |
| 3,681,684 | 8/1972 | Busker et al. | 324/640 |
| 4,902,961 | 2/1990 | De et al. | 324/640 |
| 4,947,127 | 8/1990 | Holms et al. | 73/61.43 |
| 4,977,377 | 12/1990 | Durrett et al. | 324/637 |
| 5,014,010 | 5/1991 | Helms et al. | 324/640 |
| 5,049,823 | 9/1991 | Cestel et al. | 324/640 |
| 5,101,164 | 3/1992 | Marrelli | 73/61.44 |
| 5,150,061 | 9/1992 | Castel et al. | 324/640 |
| 5,351,521 | 10/1994 | Cracknell | 73/61.44 |

*Primary Examiner*—Hezron E. Williams
*Assistant Examiner*—Daniel S. Larkin
*Attorney, Agent, or Firm*—Martin D. Hyden; Leonard W. Pojunas

[57] ABSTRACT

A method for measuring multiphase flows in a conduit using series of microwave antennae arranged around the circumference of the conduit so as to transmit microwave energy into, or detect propagated microwave energy in the conduit, the method including the steps of: transmitting microwave energy from each antenna in turn while detecting microwave energy at the non-transmitting antenna and integrating the results from all antennae so as to characterize the flow in the conduit. Apparatus for performing the method includes means for exciting each antenna in turn to transmit microwave energy into the pipe and means for detecting microwave energy at the non-transmitting antennae, and means for integrating the results from all transmitters to characterize the flow in the conduit.

19 Claims, 5 Drawing Sheets

MICROWAVE DEVICE AND METHOD FOR MEASURING MULTIPHASE FLOWS

The present invention relates to a method and apparatus for making measurements in multiphase flows using microwave techniques. In particular, the invention provides a method and apparatus for measuring volume fractions of phases in multiphase flows such as are typically encountered in producing hydrocarbon wells.

BACKGROUND OF THE INVENTION

When multiphase fluids flow in a conduit such as a pipe, the distribution of the phases is generally irregular or non-uniform in the conduit, especially where the conduit is deviated from vertical. Often one phase is flowing at a faster rate than the others. This is particularly the case where there is a gas phase and a liquid phase or when there is a continuous liquid phase with an immiscible liquid phase of different density dispersed therein. Consequently, it is desirable to know the volume fraction of each phase in the flow and the distribution of the phases in the conduit.

Various approaches have been proposed to measure volume fraction and phase distribution in multiphase flows. It is generally considered preferable that the measurement technique be non-invasive, i.e., that any sensors should be placed at the periphery of the conduit rather than being positioned in the flow itself. In cases such as flows from hydrocarbon wells, in which there is a conductive phase (water or brine) and a nonconductive phase (oil and/or gas), it has been proposed to use capacitive measurements to analyze the flow. U.S. Pat. No. 5,017,879 describes an arrangement in which electrodes are arranged around a pipe to measure the capacitance of the fluid as it flows past the electrodes. U.S. Pat. No. 5,291,791 describes a development of the technique described in U.S. Pat. No. 5,017,879 in which a series of electrodes are arranged around the pipe and are connected to a switching arrangement which controls tile function of each electrode. By controlling the switching arrangement so as to create a measurement configuration similar to that in U.S. Pat. No. 5,017,879, and continuously changing the switching arrangement, the configuration effectively rotates around the pipe. The measurements taken for each position of the configuration can then be integrated over a given number of rotations to average out variations in sensitivity of the basic configuration due to the distribution of the phases in the pipe. U.S. Pat. No. 4,074,184 proposes a somewhat different approach, again using a series of electrodes around the pipe and a switching arrangement. In this case, each electrode in turn is excited and the capacitance is measured at each of the remaining electrodes. The measurements are then integrated over a given number of "rotations" to determine the volume fraction of the phases.

Capacitive techniques using a series of electrodes around a pipe have also been proposed for tomographic flow imaging techniques in order to identify the distribution of phases within the pipe. Examples of these can be found in U.S. Pat. No. 5,130,661 and GB 2,223,850.

Insertion devices using microwave propagation have been proposed for measuring volume fractions in multiphase flows, for example in U.S. Pat. No. 5,101,163, U.S. Pat. No. 4,996,490 and GB 2,2262,807. However, these techniques are not applicable to non-invasive devices. An imaging system for active microwave tomography is proposed in "Cylindrical Geometry: A Further Step in Active Microwave Tomography", *IEEE Transactions on Microwave Theory and Theory and Techniques*, Vol. 39, No. 5, May 1991. In this system, a cylindrical arrangement of microwave antennae is described, the object to be imaged being positioned inside this arrangement. Each antenna in turn transmits microwave energy which is detected at the remaining antennas. An image of the object is reconstructed from the detected signals. There is no teaching in this document which relates to dynamic measurements such as those in flowing fluids.

The present invention seeks to provide a method and apparatus which can be used to measure multiphase flows such as those encountered from hydrocarbon producing wells.

SUMMARY OF THE INVENTION

In one aspect, the present invention provides a method for measuring multiphase flows in a conduit using series of microwave antennae arranged around the circumference of the conduit so as to transmit microwave energy into, or detect propagated microwave energy in the conduit, the method comprising: transmitting microwave energy from each antenna in turn while detecting microwave energy at the non-transmitting antenna and integrating the results from all antennae so as to characterize the flow in the conduit.

Preferably each antenna comprises a cross dipole antenna pair, typically with one dipole aligned with the axis of the conduit (the general direction of flow) and the other dipole aligned with the circumference of the conduit (perpendicular to both the axial direction and the radial direction). In this case each dipole of each pair is used in turn to transmit, and the corresponding dipoles in the other pairs are used to receive microwave energy. The antennae can be arranged in a generally planar array around the circumference of the conduit or can be spaced axially along the conduit from each other as well as circumferentially, e.g., a helical array.

The microwave energy can be transmitted at one or more frequencies for each antenna or dipole, the frequencies being selected according to the general type of flow encountered in the pipe so as to optimize the response of the technique to the flow.

In another aspect, the invention provides an apparatus for measuring multiphase flows comprising: a series of microwave antennae arranged around a flow conduit, means for exciting each antenna in turn to transmit microwave energy into the pipe and for detecting microwave energy at the non-transmitting antennae, and means for integrating the results from all transmitters to characterize the flow in the conduit.

The means for exciting each antenna can comprise a signal source and a switching arrangement for connecting the signal source to each antenna in turn while connecting the remaining antennae to a detector.

DESCRIPTION OF THE PREFERRED EMBODIMENT

Figure 1:
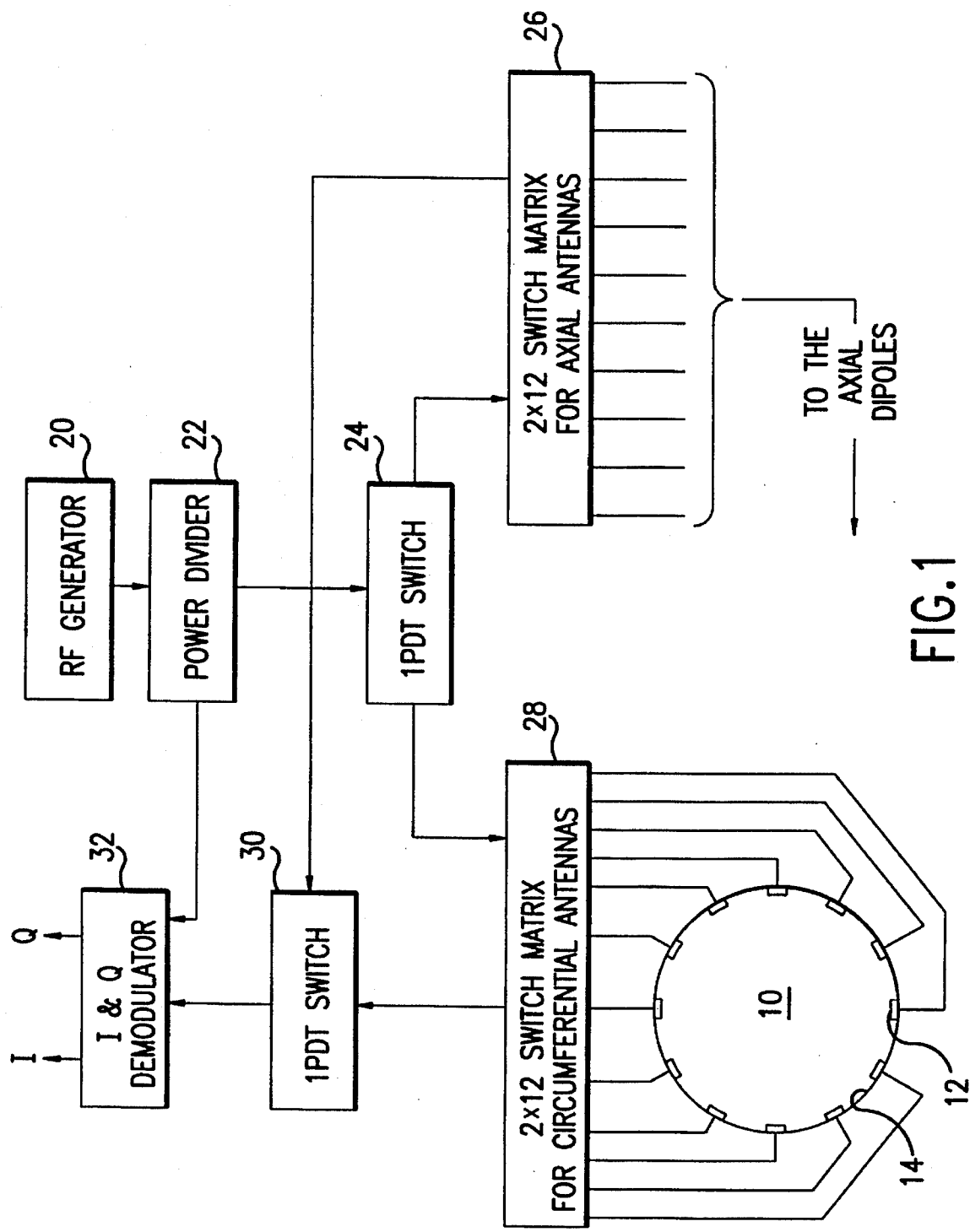
FIG. 1 shows a schematic diagram of an apparatus according to one embodiment of the invention.
Figure 2:
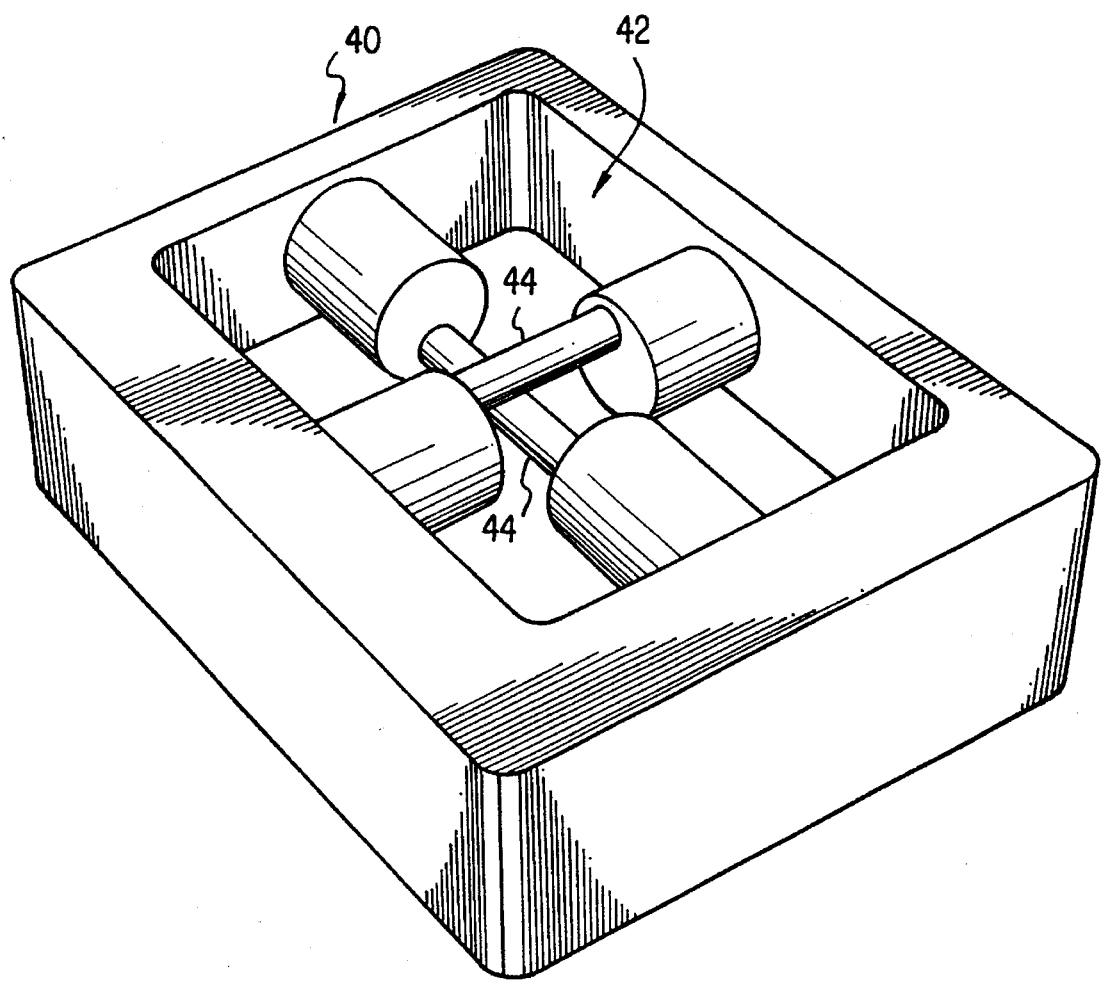
FIG. 2 shows a microwave antenna for use in the present invention.
Figure 3A:
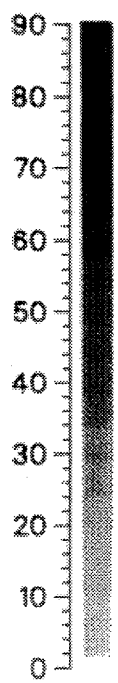
FIGS. 3a and 3b show the reconstruction of the permittivity $\epsilon$ and conductivity s/m in a pipe using calculated data from the circumferential dipole only.
Figure 3A:
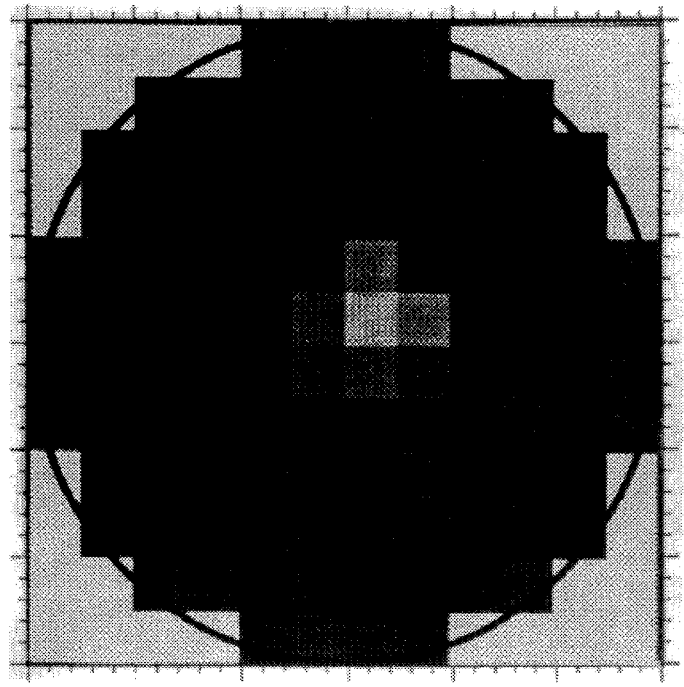
Figure 3B:
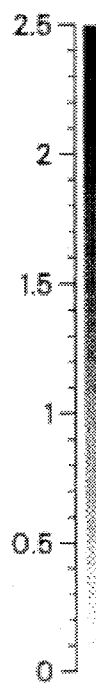
Figure 3B:
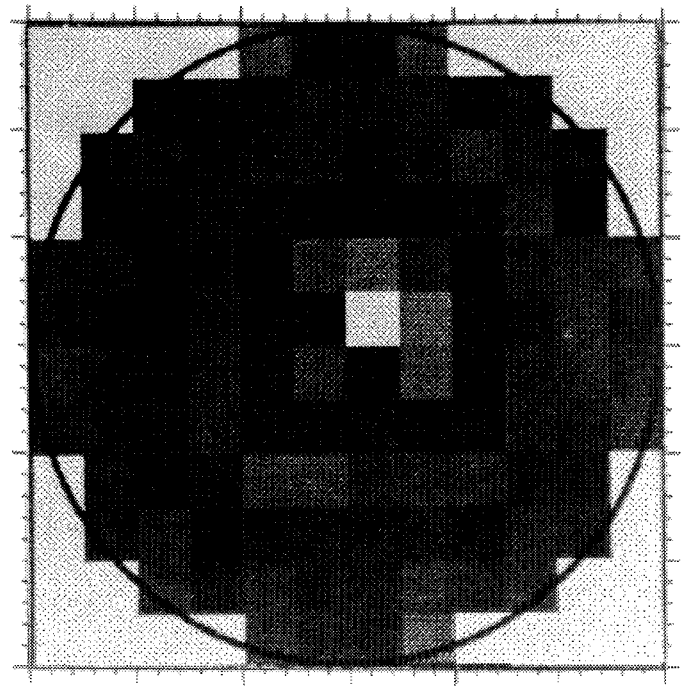
Figure 4A:
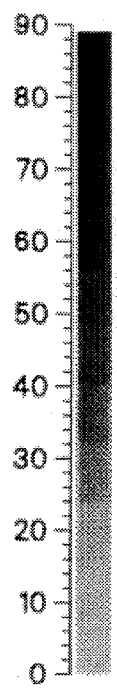
FIGS. 4a and 4b show the reconstruction of the permittivity $\epsilon$ and conductivity s/m in a pipe using calculated data from the axial dipole only.
Figure 4A:
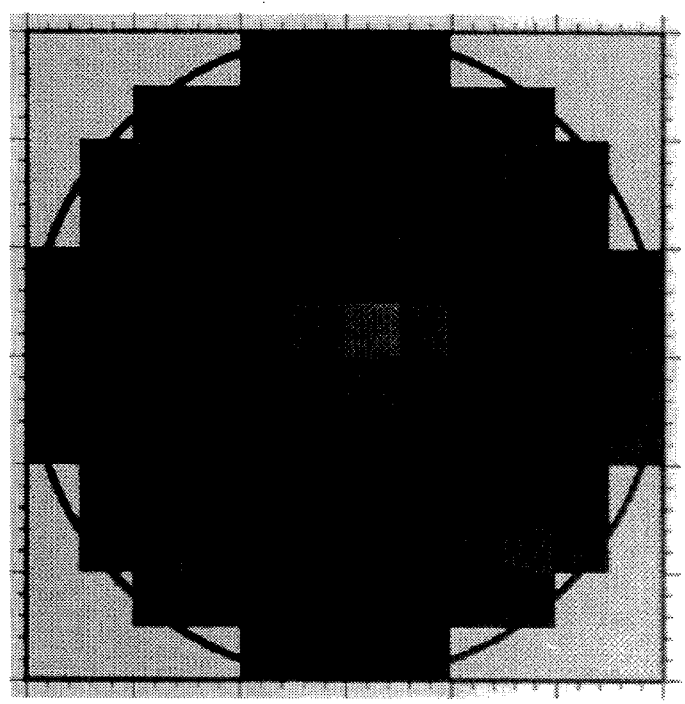
Figure 4B:
Figure 4B:
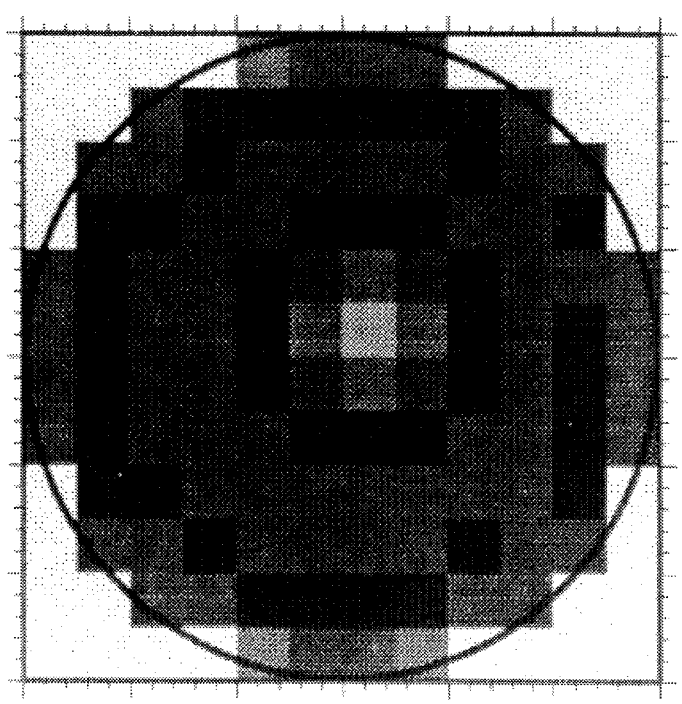
Figure 5A:
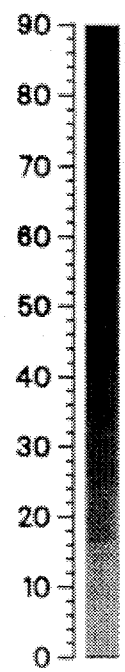
FIGS. 5a and 5b show the reconstruction of the permittivity ∈ and conductivity s/m in a pipe using both circumferential and axial measurements.
Figure 5A:
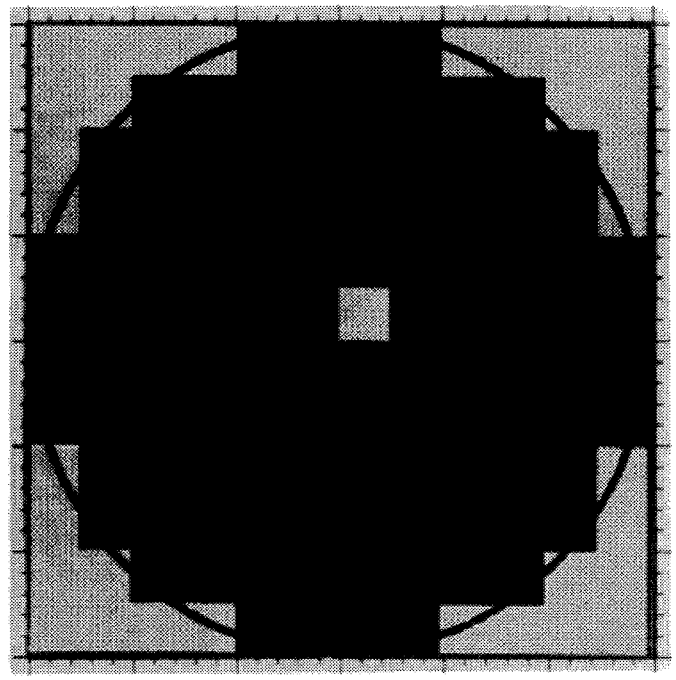
Figure 5B:
Figure 5B:
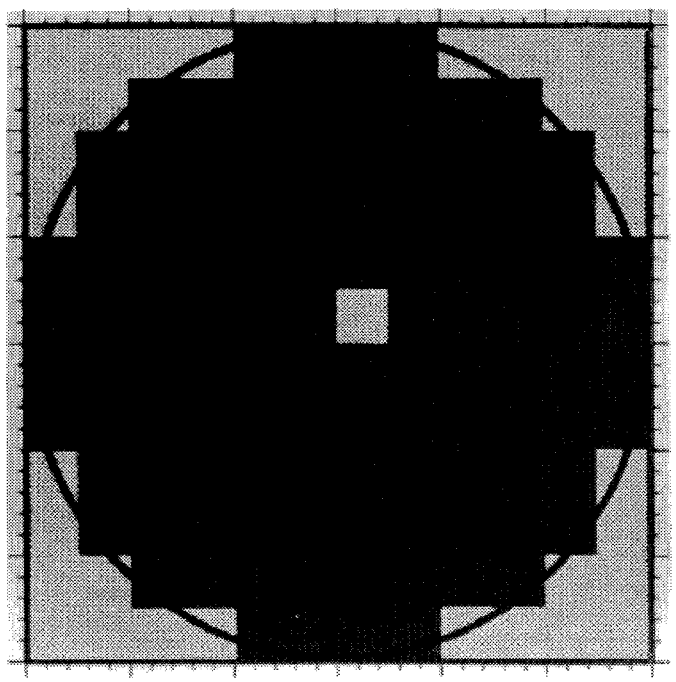

FIG. 1 shows a system according to the present invention for measuring the volume fraction of the phase in flow from a hydrocarbon well. The system comprises a pipe 10 through which the fluids flow, and a series of microwave antennae 12 mounted in the wall of the pipe 10 with radiating faces flush with the inner surface 14 of the pipe 10. In this case twelve antennae are shown although this number can be varied according to requirements. Each antenna 12 preferably comprises a crossed-dipole, cavity backed slot antenna of the type shown in FIG. 2 and described in U.S. Pat. No. 5,243,290 and Application Ser. No. 07/890,049 (both incorporated herein by reference) which disclose such antennae for use in logging underground formations. FIG. 2 shows a perspective view of a cross-dipole antenna 40 for use in this invention. The antenna 40 is a slot antenna having a square aperture 42. In the preferred embodiment, the antenna 40 operates in the range of 100 to 2000 MHz and the antenna aperture is 0.334" on each side. The antenna 40 has two perpendicular probe elements 44 (dipoles) which are centered in the aperture. Each probe element 44 is 0.063" diameter at its opposite ends. The center of each probe is narrow so the probes do not contact one another. Antennas of other dimensions are possible. These particular dimensions are one example and were chosen to yield an antenna having reasonable signal strength and acceptable resolution for borehole applications. The elements 44 could be off-centered, if desired. The antennae are arranged such that one dipole is aligned with the pipe axis so as to couple with the TE modes of the cylindrical waveguide (pipe) and The other is aligned in a circumferential direction so as to couple with the TM modes such that the antenna can radiate in two orthogonal directions. Each dipole can be operated independently to transmit or receive microwave energy. In an alternative case, both magnetic dipoles are excited simultaneously to focus the radiation. Choice of an appropriate phase and/or amplitude relationship allows the beam to be steered in a desired direction which is equivalent to exciting a combination of both TE and TM modes simultaneously which might be advantageous in certain circumstances.

The system for operating The antennae comprises an RF signal generator 20 which can output signals typically in the range 100-2000 MHz. The frequency is selected to avoid wave propagation along the pipe which means that for a 4" diameter pipe filled with oil and/or gas, i.e. a lossless fluid, the frequency should be less than 1400 MHz. When the pipe is filled with a lossless fluid, attenuation of the wave means that operation below the cutoff provides little advantage arid other advantages can be obtained by working at higher frequencies with cavity-backed slot antennae. In this case it has been found that an operating frequency in the range 500-1000 MHz ensures high antenna efficiency and operation below cutoff in lossless fluids. It is particularly preferred that the signal generator provides a number of signal frequencies, for example, two signals of different frequency can be used for a given measurement. The frequency or frequencies used can be determined by identifying the general type of flow encountered and by simple experimentation. The output from the signal generator is fed to a power divider 22. The power divider 22 feeds the signal by way of a switch 24, to either of a pair of switching matrices 26, 28.

One of the switching matrices 26 is associated with the axial dipoles of the antennae 12 and the other 28 is associated with the circumferential dipoles. The switching matrices are configured such that the RF signal is applied to each antenna 12 in turn while the remaining antennae receive transmitted microwave energy and output a signal. The output signals from the non-transmitting antennae are fed, via a further switch 30 which is set to correspond to the setting of the first switch 24, to a demodulator (I & Q demodulator) 32 which also receives a signal input from the power divider 22, i.e., a homodyne system. It is also possible to use a heterodyne detection system if desired. The demodulator 32 outputs signals indicative of the in-phase (I) and quadrature (Q) signals detected at each antenna. The in-phase and quadrature signals are used to determine the amplitude ratios and the phase shift of the detected signals with respect to the transmitted signals. The amplitude ratios (attenuation) and phase shifts are analyzed to determine the volume fraction of the phases in the pipe.

In the general case, the system comprises N antennae, one of which transmits and N−1 act as receivers measuring N−1 amplitudes and N−1 phase shifts with respect to the transmitter. This constitutes $2\{N(N-1)/2\}=N(N-1)$ independent propagation measurements, each sampling a different region of the pipe cross section. This number is doubled where crossed dipole antennae are used and where more than one frequency is used. The data obtained from these measurements is used to reconstruct the spatial distribution of the dielectric constant and conductivity of the flowing mixture over the cross-section of the pipe and hence the distribution of phases in the pipe. This can be done by tomographic techniques such as back propagation methods or by iterative inversion techniques such as those based on a Newton-type minimization approach.

In use, the switches and switching matrices are first set such that a RF signal is applied to one set of antenna dipoles, for example the axial dipoles. The associated switching matrix operates to apply the signal to the axial dipole of each antenna in turn while switching the axial dipoles of the remaining antennae to receive microwave energy which is output as a series of signals to the demodulator and analyzer. If more than one frequency is to be used, the different frequencies are applied sequentially to each antenna. Once each axial dipole has been used to transmit microwave energy into the pipe the switches are reset such that the circumferential dipoles are excited and the measurement sequence is repeated for each antenna as before. The outcome of this sequence is that a series of signals will be generated which correspond to a measurement at one or more frequencies for each dipole of each antenna measured at the corresponding dipole of each of the other antennae. The series of signals can then be analyzed using an inversion algorithm so as to determine the volume fraction of oil in the pipe at a given instant. This is demonstrated below in an example in which the signal output of a typical apparatus for a given situation is calculated and the output analyzed to give the oil volume fraction.

This example utilizes a forward model which enables one to predict the response of the apparatus, for a given known permittivity and conductivity map (i.e. oil and water distribution within the pipe) as if it were measured in the laboratory. The approach used is to discretize Maxwell's equation using a finite-difference grid. The resulting matrix equation is then solved using a band-limited matrix solver using an Lower-Upper (LU) decomposition with an iterative refinement (G. H. Golub and C. F. Van Loan, Matrix Computations, The Johns Hopkins University Press, Baltimore, Md., 1987). While calculated measurements are used in this example, the same approach can be used for real measurements.

For the reconstruction of the permittivity and conductivity maps from the (calculated) measurement, an iterative procedure is implemented whereby at each iteration step the response of the apparatus to the current iterate is compared to the (calculated) measurement. The response is computed by the abovementioned forward model using the finite-difference scheme. The residual error (also referred to as the data mismatch), defined as the difference between the measured field and the computed one, is then used to update or modify the next iterate. This update is performed using an approach referred to as the Gauss-Newton method (P. E. Gill, W. Murray, and M. H. Wright, Practical Optimization, Academic Press, Inc., Orlando, Fla., 1987). In such a scheme the minimum of the objective or cost function (defined as the length of the vector of residuals) is achieved through a line search along the steepest descent direction determined by the gradient of the cost function at the current iterate. The line search is implemented by computing an adjustable step-length along the search direction using a method by Dennis and Schnabel (J. E. Dennis and R. B. Schnabel, Numerical Methods for Unconstrained Optimization and Nonlinear Equations, Prentice Hall, Englewood Cliffs, N.J., 1983). In searching for the minimum of the cost function, the values of the permittivities and conductivities are constrained to be within their physical bounds of unity to 84 for the permittivity and 0 to 20 S/m for the conductivity. Unity permittivity corresponds to gas whereas 84 is the maximum permittivity of water. The range of 0 to 20 S/m covers the range of lossless hydrocarbons to fully salt saturated water.

To safeguard against cases where the measurement are weakly independent, we implement the Gauss-Newton approach regularized with a Levenberg-Marquardt method (P. E. Gill, W. Murray, and M. H. Wright, Practical Optimization, Academic Press, Inc., Orlando, Fla. 1987). Such a regularization method helps to suppress the magnification of noise, which is unavoidably present in the measurement.

The iterative procedure is started with an initial guess which is estimated from an effective homogeneous fluid whose permittivity and conductivity best match the measurement. The presented example is for the case of an oil bubble embedded in a metallic pipe of radius 3.5 inches filled with saline water. The oil bubble has a permittivity of 2 and a conductivity of 0 S/m. The bubble has a square shape with dimensions 7.5×7.5 mm. The bubble is located 5.25 mm away from the center of the pipe along the 45 degree line. The water has a permittivity of 78 and a conductivity of 2 S/m. The measurement is simulated at a frequency of 800 MHz. It constitutes both real and imaginary parts of the voltage measured by the cavity backed slot antennas for axial and circumferential polarizations. The measurement is simulated for 12 antenna locations uniformly distributed on the surface of the pipe. The total number of measurements is, therefore, 132 complex-valued voltages (or 264 in-phase and quadrature voltages corresponding to the real and imaginary parts of the complex-valued voltages) for both polarizations or 66 complex-valued voltages for each polarization.

Since there are only 132 complex-valued voltages available for mapping the permittivity and conductivity of the fluid inside the pipe, this determines the number of pixels or cells which one can divide the cross-section of the pipe for the system to be evenly determined. To allow for redundancy in data, we have divided the pipe into 112 cells rendering the system an over-determined one. The diameter of the pipe and the number of antennas determine the number of cells which can be selected to allow the system to remain overdetermined and hence the resolution of the apparatus In FIGS. 3-5 the values of permittivity $\epsilon$ and conductivity (s/m) are plotted for each cell as a shade of gray in accordance with the palettes shown. In normal use only a combined image (FIG. 5) would be used and it is possible to determine the volume fraction without using an image at all by means of a suitably programmed computer. FIG. 3 shows the reconstruction of the permittivity (FIG. 3a) and conductivity (FIG. 3b) using calculated data from axial dipole measurements alone whereas FIG. 4 shows the reconstruction of the permittivity (FIG. 4a) and conductivity (FIG. 4b) using calculated data from circumferential dipole measurements alone. In either of these two cases, we have an under-determined system since the number of measurements is 66 while the number of the unknowns (cells) is 112. It is clear from these reconstructions that the obtained image is a blurred one because of the deficiency in measurement. FIG. 5 shows the reconstruction using both axial and circumferential measurements rendering the system over-determined. In this case we get an almost perfect rendition of the oil bubble.

Not only does the present invention allow the value fractions of the phases to be determined at a given instant, the ability to form an image allows the type of flow to be characterized as well, e.g., bubble flow, slug flow, churn flow, annular flow, wispy annular flow etc. Also, measurements can be made cautiously and sporadically depending on the amount and type of information required and the integration period required for accurate measurements.

We claim:

1. A method for measuring multiphase flows in a conduit comprising using series of microwave antennae arranged around the conduit, each antenna being capable of transmitting microwave energy into the conduit and detecting propagated microwave energy in the conduit, transmitting microwave energy from each antenna in turn while detecting said microwave energy at the antennae which are not transmitting after propagation in the conduit so as to generate output signals; and integrating the output signals from all antennae so as to measure the flow in the conduit.

2. A method as claimed in claim 1, wherein each antenna comprises a crossed dipole antenna pair.

3. A method as claimed in claim 2, wherein one dipole is aligned with the direction of flow in the conduit and the other dipole aligned perpendicularly to both the direction of flow and the radial direction.

4. A method as claimed in claim 3, wherein each dipole of each pair is used in turn to transmit microwave energy into the conduit, and the corresponding dipoles in the other pairs are used to receive the propagated microwave energy.

5. A method as claimed in claim 2, wherein the microwave energy is transmitted at one or more frequencies for each antenna or dipole, the method comprising selecting the frequencies according to the general type of flow encountered in the conduit so as to optimize the measurement of the flow.

6. A method as claimed in claim 1, comprising forming an image from the output signals and characterizing the flow therefrom.

7. A method as claimed in claim 1, comprising repeating the measurements so as to obtain a time series of output signals for integration.

8. A method as claimed in claim 1, wherein microwave energy is transmitted from each antenna for a period selected to optimize generation of output signals.

9. Apparatus for measuring multiphase fluid flows comprising: a flow conduit through which said multiphase fluid flows, a series of microwave antennae arranged around the flow conduit, means for exciting each antenna in turn to transmit microwave energy into the conduit, means for detecting microwave energy propagated in the conduit at the antennae which are not transmitting and for producing output signals, and means for integrating the output signals from all antennae to measure flow in the conduit.

10. Apparatus as claimed in claim 9, wherein each antenna comprises a crossed dipole antenna pair.

11. Apparatus as claimed in claim 10, wherein one dipole is aligned with the direction of flow in the conduit and the other dipole aligned perpendicularly to both the direction of flow and the fatal direction.

12. Apparatus as claimed in claim 11, wherein the means for exciting each antenna excites each dipole of each pair in turn to transmit microwave energy into the conduit, and the means for detecting microwave energy propagated in the conduit detects the propagated microwave energy at corresponding dipoles in antennae which are not transmitting to generate output signals.

13. Apparatus as claimed in claim 9, wherein the means for exciting each antenna in turn causes microwave energy to be transmitted at least one frequency for each antenna according to the general type of flow encountered in the conduit so as to optimize the measurement of the flow.

14. Apparatus as claimed in claim 10, wherein the means for exciting each antenna in turn causes microwave energy to be transmitted at least one frequency for each dipole according to the general type of flow encountered in the conduit so as to optimize the measurement of the flow.

15. Apparatus as claimed in claim 9, wherein the means for exciting each antenna comprises a signal source, a detector and a switching arrangement for connecting the signal source to each antenna in turn while connecting the antennae which are not transmitting to a detector.

16. Apparatus as claimed in claim 15, wherein each antenna comprises a crossed dipole antenna pair and the switching arrangement connects the signal source to one dipole of each pair in turn while connecting the corresponding dipoles of the antennae which are not transmitting to the detector.

17. Apparatus as claimed in claim 16, wherein one dipole of each pair is aligned with the direction of flow in the conduit and the other dipole aligned perpendicularly to both the direction of flow and the radial direction.

18. Apparatus as claimed in claim 17, wherein the switching arrangement connects the signal source to each dipole aligned in one direction in turn for all antennae and then connects the signal source to each dipole aligned in the other direction in turn for all antennae.

19. Apparatus for measuring multiphase flows comprising:

a) a series of microwave antennae arranged around a flow conduit, each antenna comprising a crossed dipole pair, one dipole of the pair being aligned with the direction of flow and the other dipole being aligned perpendicularly to both the direction of flow and the radial direction, b) means for separately exciting the dipoles of each antenna pair in turn to transmit microwave energy into the conduit, c) means for detecting microwave energy propagated in the conduit at the corresponding dipoles which are not transmitting and for producing output signals, and d) means for integrating the output signals from all dipoles to measure flow in the conduit.

\* \* \* \* \*